United States Patent [19]
Honaker et al.

[11] Patent Number: 5,833,093
[45] Date of Patent: Nov. 10, 1998

[54] PROTECTIVE COVER FOR SMALL SPRAY DISPENSERS AND MEDICATED INHALERS

[76] Inventors: Denise Honaker, 22716 Kathryn Ave., Torrance, Calif. 90505; Diana Brettrager, 145 Poppy Ave., Monrovia, Calif. 91016

[21] Appl. No.: 610,437

[22] Filed: Mar. 4, 1996

[51] Int. Cl.⁶ .................................................. B67D 5/64
[52] U.S. Cl. ................ 222/175; 222/179.5; 222/182; 222/192; 224/148.5; 224/148.6; 224/251; 224/269
[58] Field of Search ............................. 222/175, 179.5, 222/182, 192; 224/148.5, 148.6, 250, 251, 269

[56] References Cited

U.S. PATENT DOCUMENTS

| | | | |
|---|---|---|---|
| 3,450,313 | 6/1969 | Jonas | 222/175 X |
| 4,509,515 | 4/1985 | Althounyan et al. | 222/179.5 X |
| 4,967,986 | 11/1990 | Schildkraut | 224/250 |
| 5,060,835 | 10/1991 | Payne | 224/148.6 X |
| 5,215,227 | 6/1993 | Farner | 222/175 |
| 5,325,991 | 7/1994 | Williams | 224/148.5 X |
| 5,337,907 | 8/1994 | McKenzie et al. | 224/148.5 X |
| 5,443,192 | 8/1995 | Hodges et al. | 224/148.6 |
| 5,566,869 | 10/1996 | Katz | 224/148.6 |

*Primary Examiner*—Joseph Kaufman
*Attorney, Agent, or Firm*—Pretty, Schroeder & Poplawski

[57] ABSTRACT

A protection cover for small spray dispensers including a rectangular base of a flexible material that can be folded on itself to form a closed cover and define a dispenser space. The base has an outer surface and an inner surface with the hook-and-loop patches carried at each end of the base for interengaging each other for latching the base in the closed cover form. The information card retainer on the inner surface of the base, including a transparent sheet of flexible material attached to the base, with an open side for insertion and removal of a card and a sleeve of a flexible material carried on the inner face of the base.

2 Claims, 3 Drawing Sheets

FIG. 4
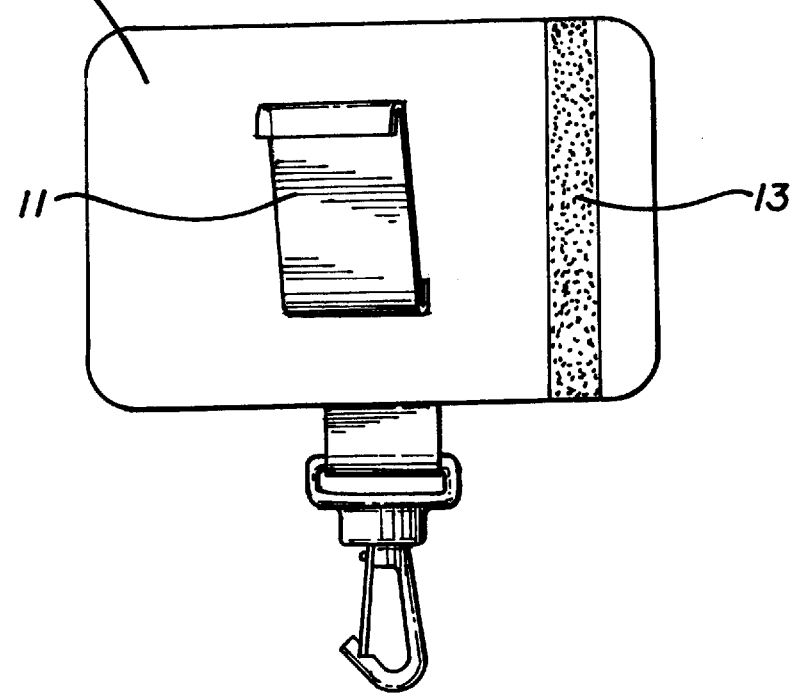
FIG. 3
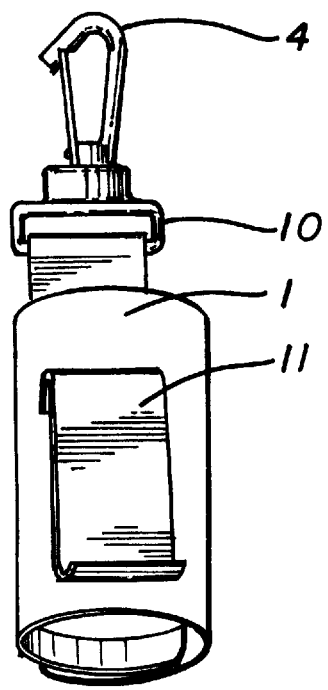
FIG. 5

000000
PROTECTIVE COVER FOR SMALL SPRAY DISPENSERS AND MEDICATED INHALERS

BACKGROUND OF THE INVENTION

The present invention relates in general to protective covers and in particular to protective covers for asthma and allergy inhalers and spray dispensers.

The most common problem with asthma and allergy medication is availability of the inhaler dispenser. Kids who make up the bulk of the users are constantly loosing their inhalers. Inhalers are small and easy to loose not only for kids but adults too. People are getting tired of fishing for their dispensers out of the bottom of purses or briefcases. And what if you need to get your medication during an attack? Of course you'll want your medicine quickly and easy to find. And if you can make it more fun for kids, then they'll be less likely to forget to purposely leave that inhaler at home. This invention will make all types of inhalers easy to carry, make medication quickly accessible, will help keep inhalers clean, help prevent accidental discharge and will make inhaler medication a fun necessity for kids.

SUMMARY OF THE INVENTION

The principle object of the present invention is to provide a device that quickly enables asthma and allergy sufferers access to their medication, to help prevent inhaler loss and to encourage children to carry and take their own medication.

It is also an object to provide such a device which, in use, can be attached to clothing, key rings, kids backpacks and a variety of other surfaces.

A further object is to provide an easily opened case that also keeps the inhaler protected from the elements.

Another object is to provide personal emergency information with the device.

The foregoing objects can be accomplished by providing an inhaler holder made of a rectangular sheet of flexible material. This rectangular sheet is of sufficient length to completely wrap around the spray dispenser and is secured with hook-and-loop material.

An information compartment consisting of a transparent material, acts like a small picture frame holding a personal information card.

A clip attached to the rectangular sheet provides attachment opportunities to a variety of surfaces.

BRIEF DESCRIPTION OF THE DRAWINGS

FIG. 3 is a front view of the device in its folded stage with a spray dispenser stored inside;

FIG. 4 is a view of the exterior of the device opened;

FIG. 5 is a side view of the "S" clip;

DESCRIPTION OF THE PREFERRED EMBODIMENTS

Figure 1:
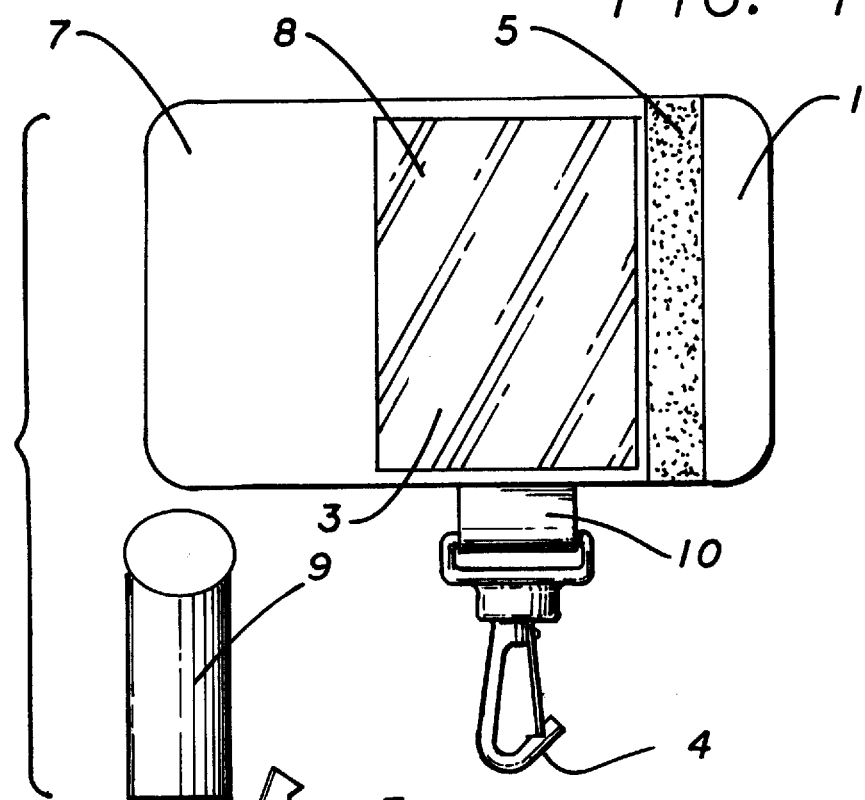
FIG. 1 is a view of the interior surface of the device opened.

Referring to the drawing figures and to FIG. 1 and FIG. 4 in particular, the device consists of a rectangular base 1, of flexible, collapsible material, such as nylon. It has a width sufficient in length to encircle a variety of inhaler dispensers when in the folded FIG. 3 position. The rectangular base is secured in the folded position with hook-and-loop material 5 (FIG. 1), affixed by stitching to the interior surface of said base, and hook-and-loop material 13 (FIG. 4) on the exterior of said base, also affixed by stitching. The rectangular sheet and its components, including the inhaler dispenser, is wrapped into position as shown in FIG. 3. The wrapped position protects the inhaler 9 from damage, dirt, and accidental discharge. Spray dispensers may be secured to the rectangular base, with the pocket type holder 2 or looped strap holder 14 or twin strap holder 15 or twin pocket type dispenser holders 2, or wrapped in the rectangular base 1 without any strap or pocket type holders.

Figure 2:
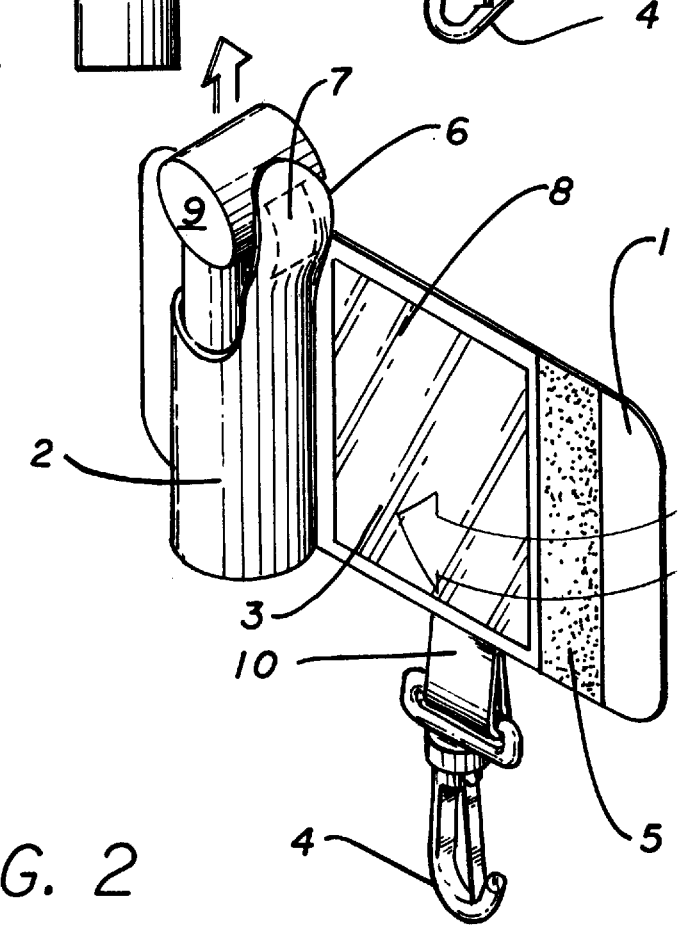
FIG. 2 is a isometric view of the interior surface of the device with the spray dispenser partially removed from the pocket type dispenser holder.
Figure 6:
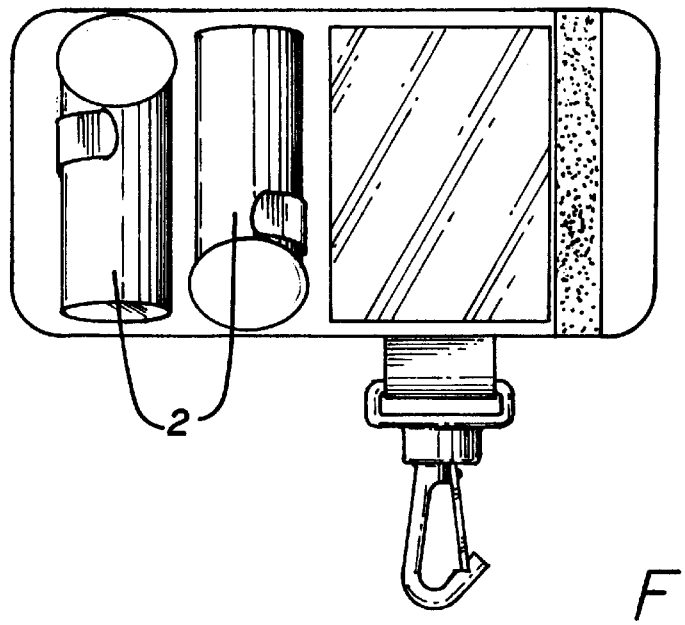
FIG. 6 is a view of the interior surface of the device opened, with two pocket-type dispenser holders.

With regard to FIG. 2, the pocket type dispenser holder 2, is constructed of the same flexible, collapsible material as the rectangular base 1. The pocket type dispenser holder consists of a tubular design sufficient in size to enclose a variety of spray dispensers. The pocket type dispenser is affixed by stitching to the interior of rectangular base 1. Flap 6 secures the inhaler 9 in place by means of hook-and-loop material 7 stitched into the interior of flap 6 and with the mating hook-and-loop material stitched to the exterior of the pocket type dispenser holder.

The flexibility of the material of flap 6 allows users to apply pressure to the top of the stray dispenser by pressing down on flap 6 for discharge without removing the spray dispenser from the pocket type holder and without folding back flap 6. Also, spray dispensers can be removed from the pocket type dispenser holder 2, for replacement or for personal use, by easily removing flap 6 from its hook-and-loop connectors.

Figure 7:
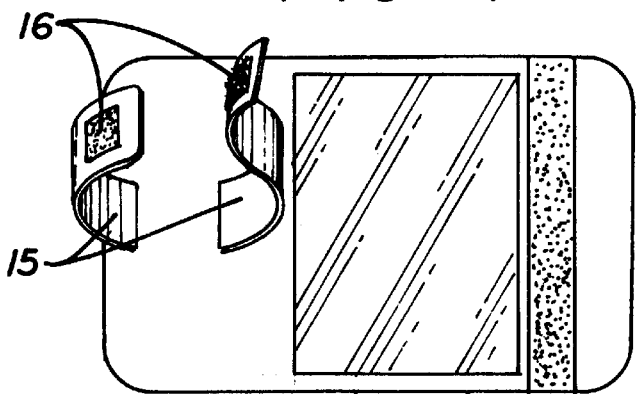
FIG. 7 is a view of the interior surface of the device opened, with a strap type holder joined with hook and loop material.

Referring to FIG. 7, twin strap holder 15, consists of two straps of sufficient length to encircle a variety of stray dispensers and are stitched into the interior of rectangular base 1. Hook-and-loop materials 16, affixed by stitching, secure the two straps around the inhaler dispenser.

Figure 8:
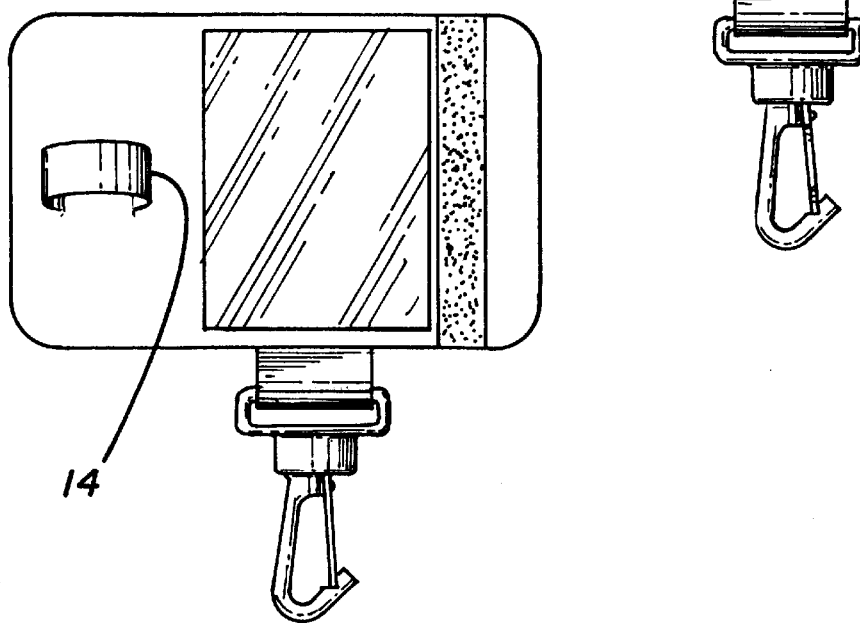
FIG. 8 is a view of the interior surface of the device opened, with a looped strap type holder.

Referring to FIG. 8, looped strap holder 14, is affixed to the interior of rectangular base 1 with stitching. Looped strap 14 is of an elastic material for accommodating inhaler dispensers of varying diameters.

Affixed by stitching on three sides, transparent information compartment 8 allows for quick viewing of the information card 3 contained within the compartment and protects the card from damage. Compartment 8 consists of a flexible transparent material such as thin gauge plastic affixed to the interior of the rectangular base 1 by stitching on three sides and is open ended on one side to allow for insertion or removal of the information card.

Snap hook hanger 10 consists of nylon strapping which is passed through snap hook 4 and is connected to a side edge of rectangular base 1 by stitching. Snap hook 4 allows easy transportation of inhaler 9 by attaching to a variety of surfaces and clothing. This helps in the prevention of loss by users, and allows for quick access to their dispensers. Users can hook the entire device to their own preferred areas for quick access of medication and not hunt around for their dispenser.

Referring to FIGS. 3 and 5, a rigid "S" shaped clip 11 also enables securement of the holder to many items such as belts or over a waistband of a joggers running shorts.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

We claim:

1. A protection cover for small spray dispensers including in combination:

a rectangular base of a flexible material that can be folded on itself to form a closed cover and define a dispenser space therein, said base having an outer surface and an inner surface;

hook-and-loop patches carried at each end of said base for interengaging each other for latching said base in said closed cover form;

an information card retainer on said inner surface of said base, said retainer including a transparent sheet of flexible material attached to said base, with an open side for insertion and removal of a card;

a sleeve of a flexible material carried on said inner face of said base, said sleeve being tubular in shape with a closed bottom and side and an open top, and with an integral closure flap at said open top, said sleeve flap having hook and loop fastening patches for closing said open top by said closure flap;

a second sleeve of a flexible material carried on said inner surface of said base, said second sleeve being tubular in shape with a closed bottom and side and an open top, and with an integral closure flap at said open top, said second sleeve flap having hook and loop fastening patches for closing said open top by said closure flap, said second sleeve being oriented on said base in a position inverted to that of the initial sleeve; and connection means carried on said base for connecting said protective cover to a support member.

2. A protection cover as defined in claim 1 wherein said connection means includes a rigid "S" shaped clip affixed to the exterior of said rectangular base.

* * * * *